United States Patent
Abeliuk et al.

(10) Patent No.: US 12,293,306 B2
(45) Date of Patent: *May 6, 2025

(54) METHOD, APPARATUS, AND COMPUTER-READABLE MEDIUM FOR EFFICIENTLY OPTIMIZING A PHENOTYPE WITH A SPECIALIZED PREDICTION MODEL

(71) Applicant: TeselaGen Biotechnology Inc., San Francisco, CA (US)

(72) Inventors: Eduardo Abeliuk, Palo Alto, CA (US); Juan Andrés Ramírez Neilson, Santiago (CL); Andrés Igor Pérez Manríquez, Santiago (CL); Diego Francisco Valenzuela Iturra, Santiago (CL)

(73) Assignee: TESELAGEN BIOTECHNOLOGY INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,158

(22) Filed: Apr. 3, 2023

(65) Prior Publication Data

US 2024/0054365 A1 Feb. 15, 2024

Related U.S. Application Data

(63) Continuation of application No. 16/725,642, filed on Dec. 23, 2019, now Pat. No. 11,620,544.

(Continued)

(51) Int. Cl.
*G06F 17/00* (2019.01)
*G06N 5/04* (2023.01)
(Continued)

(52) U.S. Cl.
CPC ............... *G06N 5/04* (2013.01); *G06N 20/00* (2019.01); *G16B 20/00* (2019.02); *G16B 40/00* (2019.02)

(58) Field of Classification Search
CPC ............ G06N 5/04; G06N 5/01; G06N 20/00; G06N 20/20; G06N 3/044; G06N 3/045;
(Continued)

(56) References Cited

U.S. PATENT DOCUMENTS 10,249,389 B2 * 4/2019 Athey ..................... G16H 10/60
10,437,858 B2 * 10/2019 Naughton ............. G16B 50/00
(Continued)

*Primary Examiner* — Greta L Robinson
(74) *Attorney, Agent, or Firm* — Reed Smith LLP; Amardeep S. Grewal

(57) ABSTRACT

A method, apparatus, and computer-readable medium for efficiently optimizing a phenotype with a specialized prediction model, including receiving constraints, encoding genotype information in experimental data points corresponding to the constraints experiential genotype vectors, the experimental data points comprising the genotype information and phenotype information corresponding to the genotype information, training a phenotype prediction model based on the experiential genotype vectors, the corresponding phenotype information, and the one or more constraints, applying the phenotype prediction model to available genotypes corresponding to the constrains to generate scores, determining result genotypes based on a ranking of the available genotypes according to the scores, and generating, a result based on the result genotypes, the result indicating one or more genetic constructs for testing.

21 Claims, 11 Drawing Sheets

Related U.S. Application Data

(60) Provisional application No. 62/784,101, filed on Dec. 21, 2018.

(51) Int. Cl.
*G06N 20/00* (2019.01)
*G16B 20/00* (2019.01)
*G16B 40/00* (2019.01)

(58) Field of Classification Search
CPC .......... G06N 7/01; G16B 20/00; G16B 40/00; G16B 40/20
See application file for complete search history.

(56) References Cited

U.S. PATENT DOCUMENTS

| | | | |
|---|---|---|---|
| 11,620,544 B2* | 4/2023 | Abeliuk | G16B 40/20 706/12 |
| 2007/0027636 A1* | 2/2007 | Rabinowitz | G16B 20/00 705/2 |
| 2016/0132635 A1* | 5/2016 | Buntjer | A01K 67/02 702/20 |
| 2017/0169160 A1* | 6/2017 | Hu | C12Q 1/6876 |
| 2019/0042697 A1* | 2/2019 | Kiel | G16B 50/00 |
| 2019/0180842 A1* | 6/2019 | Leonardi | G16B 40/20 |
| 2020/0135300 A1* | 4/2020 | Mishne | G16B 20/00 |
| 2021/0257049 A1* | 8/2021 | Abeliuk | G06N 3/045 |

* cited by examiner

METHOD, APPARATUS, AND COMPUTER-READABLE MEDIUM FOR EFFICIENTLY OPTIMIZING A PHENOTYPE WITH A SPECIALIZED PREDICTION MODEL

RELATED APPLICATION DATA

This application is a continuation of U.S. Nonprovisional application Ser. No. 16/725,642 filed Dec. 23, 2019, and titled "METHOD, APPARATUS, AND COMPUTER-READABLE MEDIUM FOR EFFICIENTLY OPTIMIZING A PHENOTYPE WITH A SPECIALIZED PREDICTION MODEL", which claims priority to U.S. Provisional Application No. 62/784,101, filed Dec. 21, 2018, and titled "METHOD, APPARATUS, AND COMPUTER-READABLE MEDIUM FOR GENERATING AND ADJUSTING A PREDICTIVE MODEL CONFIGURED TO OPTIMIZE THE PHENOTYPE OF A BIOLOGICAL SYSTEM," the disclosure of which is hereby incorporated by reference in its entirety.

BACKGROUND

A recurrent problem in synthetic biology is to find the genetic sequence that optimizes, for a given biological system, the production of a specific molecule or compound, or more generally that optimizes a specific metric that characterizes the phenotype of a given biological system. In general this search can be quite expensive because it requires numerous experiments. Evaluating the performance and characterizing the phenotype of different genetic variants can consume a lot of time and resources.

Instead of searching for an optimal genetic design within the universe of all possible genetic sequences, it becomes important to focus the search to certain known variants of genes or parts of DNA directly involved in the production of the compound, or phenotype of the corresponding biological system. Despite the narrowing of the search space to be explored, the number of possible genetic designs is typically quite large and it is necessary to have tools that allow finding the optimal genetic design with the smallest number of experiments as possible.

Unfortunately, even with a reduced search space, it is completely unfeasible for a geneticist to implement and collect results from even a small fraction of the possible genetic designs, as the number of combinatorial possibilities scales exponentially according to the number of component genotype variants.

Additionally, attempts to reduce the search space using automated techniques and algorithms are also impractical due to both the exponential computational complexity of the search problem and the difficulty in quantifying the phenotype expressions for genotype sequences which have not previously been assessed experimentally.

Accordingly, improvements are needed in technology for predictive modeling of the phenotype of a biological system and efficiently optimizing a phenotype.

DETAILED DESCRIPTION

While methods, apparatuses, and computer-readable media are described herein by way of examples and embodiments, those skilled in the art recognize that methods, apparatuses, and computer-readable media for efficiently optimizing a phenotype with a specialized prediction model are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "can" is used in a permissive sense (i.e., meaning having the potential to) rather than the mandatory sense (i.e., meaning must). Similarly, the words "include," "including," and "includes" mean including, but not limited to.

As discussed above, while running new experiments to optimize the phenotype of the biological system (such as the titer of a metabolite), it would be useful to have a system that optimizes the phenotype of a biological system based on experimental data previously obtained and that also reduces the computational complexity of the search problem so that a possible solution set can be determined in a feasible time. Researchers would then have additional information that would allow them to make better decisions regarding which experiments to perform.

Applicant has discovered a method, apparatus, and computer-readable medium for efficiently optimizing a phenotype with a specialized prediction model. The specialized prediction model is constructed specifically to optimize the phenotype of a biological system by generating phenotype predictions relating to genotypes which have not been experimentally characterized and which meet a user's requirements. The disclosed method, apparatus, and computer-readable medium are further configured to reduce the computational complexity of exploring the search space of possible genotypes using a variety of specialized heuristics adapted to this domain and, in some cases, adapted to the hardware that is used to apply the prediction model.

Figure 1:
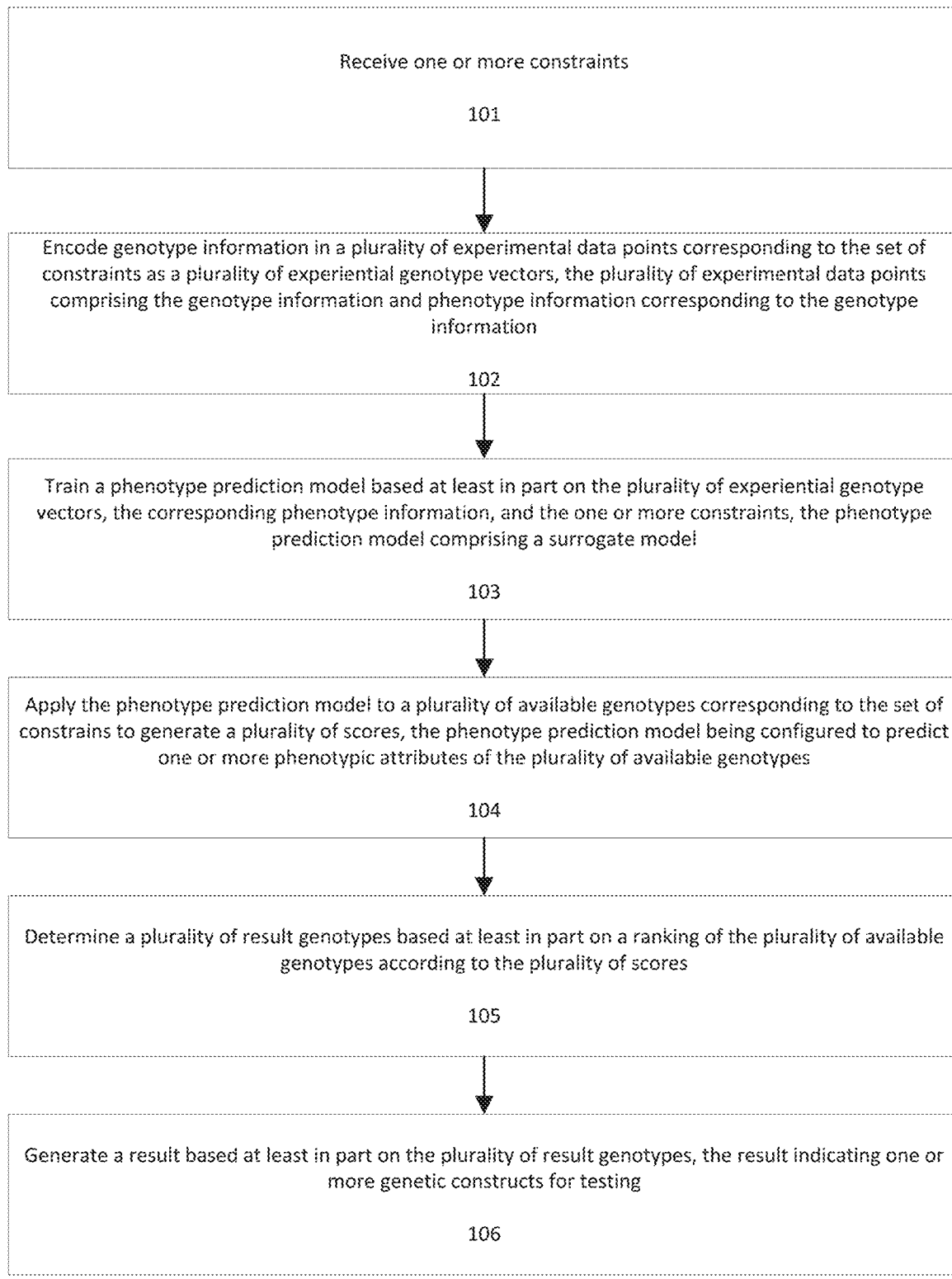
FIG. 1 illustrates a flowchart for efficiently optimizing a phenotype with a specialized prediction model according to an exemplary embodiment.

FIG. 1 illustrates a flowchart for efficiently optimizing a phenotype with a specialized prediction model according to an exemplary embodiment.

At step 101 one or more constraints are received. The one or more constraints are constrains particular to a specific user's goals, experimental conditions, limitations, or other factors relating to the desired output from the predictive model. The one or more constraints can include a plurality of available genotypes and/or a plurality of desired phenotypic attributes. The plurality of available genotypes can correspond to the genotypes that a particular user is able to create or has access to for experimental purposes. Additionally, the plurality of desired phenotypic attributes correspond to the phenotypes that a user is seeking to optimize through use of the system and subsequent experimentation.

One of skill in the art will of course understand that genotype refers to a genetic constitution or sequence and phenotype refers to an observable characteristic resulting from the interaction of a genotype with a particular environment. A phenotype can include, for example, the ability of a particular genotype to produce a specified molecule, compound or metabolite (determined by the titer of the molecule), bacterial growth (determined by optical density data), resistance of a strain to extreme conditions and temperature, salinity, or pH conditions, etc.

The constraints can be received from a user via an input interface or in a communication via a network interface. The constraints can also be received from a software process or computing system via a messaging protocol, a network connection, or other communication mechanism.

The step of receiving the constraints can include the user specifying the pool of variants that should be explored for each bin. The user can use just the labels or, alternatively, the genetic/amino-acid sequences if using a sophisticated embedding approach. The user also needs to specify the property to be optimized (this means that the user has to provide, for example, the name of the column that contains the target value in the database). The algorithm will always try to maximize that phenotypic value, so the user should be aware of that and perform a transformation on the property if required to obtain a benefit from the process. A common transformation is, for example, multiplying all values by −1 in order to minimize the original phenotype measurement.

At step 102 genotype information in a plurality of experimental data points corresponding to the set of constraints is encoded as a plurality of experiential genotype vectors, the plurality of experimental data points comprising the genotype information and phenotype information corresponding to the genotype information.

This step can include, for example, interfacing and communicating with experimental database storing all experimental data points and extracting the plurality of experimental data points that correspond to the set of constraints. The experimental database can be a distributed database, such as a cloud database, that is accessible to a plurality of researchers. Each researcher can then upload experimental results to the database in order to provide additional training data for training the model, as will be discussed further below.

Each experimental data point can include phenotypic measurements and corresponding genotype data. For example, the experimental data point can include corresponding to a particular genetic sequence, gene, and/or gene fragment and can also include phenotypic measurements that correspond to that particular genetic sequence, gene, and/or gene fragment. The phenotypic measurements can be measurements that were experimentally determined in previous experiments. The experimental data points can be configured to link genotype data with phenotypic measurements in a memory of the database, such as through a relational database, directed graph, or other techniques.

Optionally, this step can include encoding all genotype information in the plurality of experimental data points as a plurality of experiential genotype vectors, irrespective of the constraints. For example, when the experimental dataset is small (say a few hundred constructs), all of these constructs can be used to generate the plurality of experiential genotype vectors.

Figure 2:
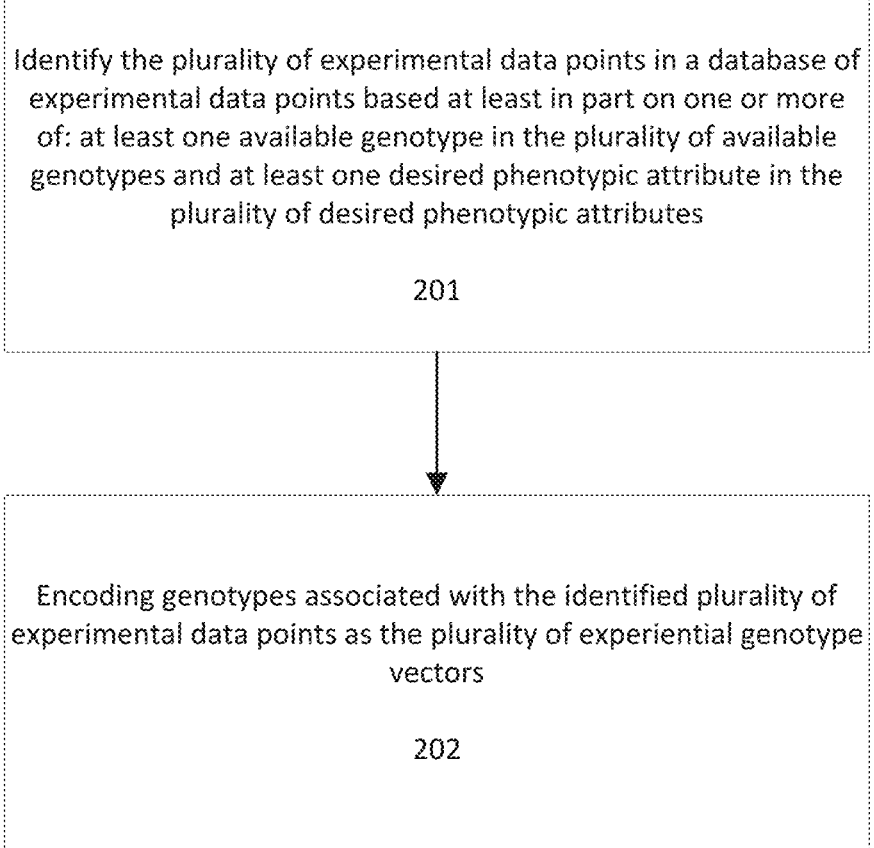
FIG. 2 illustrates a flowchart for encoding genotype information in a plurality of experimental data points corresponding to the set of constraints as a plurality of experiential genotype vectors according to an exemplary embodiment.

It only contains the experiments that the scientists have already performed in the lab. This group of samples is a subset of all the possible candidates that you can build if you recombine the alleles (variants) that are present on those constructs. Thus, the group of all possible candidates is bigger, and can contain thousands or hundreds of thousands candidates FIG. 2 illustrates a flowchart for encoding genotype information in a plurality of experimental data points corresponding to the set of constraints as a plurality of experiential genotype vectors according to an exemplary embodiment.

At step 201 the plurality of experimental data points are identified in a database of experimental data points based at least in part on one or more of: at least one available genotype in the plurality of available genotypes and at least one desired phenotypic attribute in the plurality of desired phenotypic attributes. This step can conduct a search of the database for all experimental data points that have genotypes matching or interchangeable with at least one genotype listed in the plurality of available genotypes. This step can also conduct a search of the database for all experimental data points that have phenotypic measurements matching at least one desired phenotypic attributes in the plurality of desired phenotypic attributes. As discussed earlier, phenotypic attributes can include, for example, the ability of a genotype to produce a specified molecule or compound.

At step 202 the genotypes associated with the identified plurality of experimental data points are encoded as a plurality of experiential genotype vectors. This encoding process is discussed in greater detail below. Of course, the genotypes associated with the identified plurality of experimental data points can be encoded in other ways, such as by representing the genotypes using a categorical or nominal representation correspond to categories/sequences/sub-sequences, etc. As part of the encoding process, the phenotypic measurements in the identified plurality of experimental data points can optionally also be encoded using one or more of the above-described schemes to later enable more efficient analysis.

Figure 3:
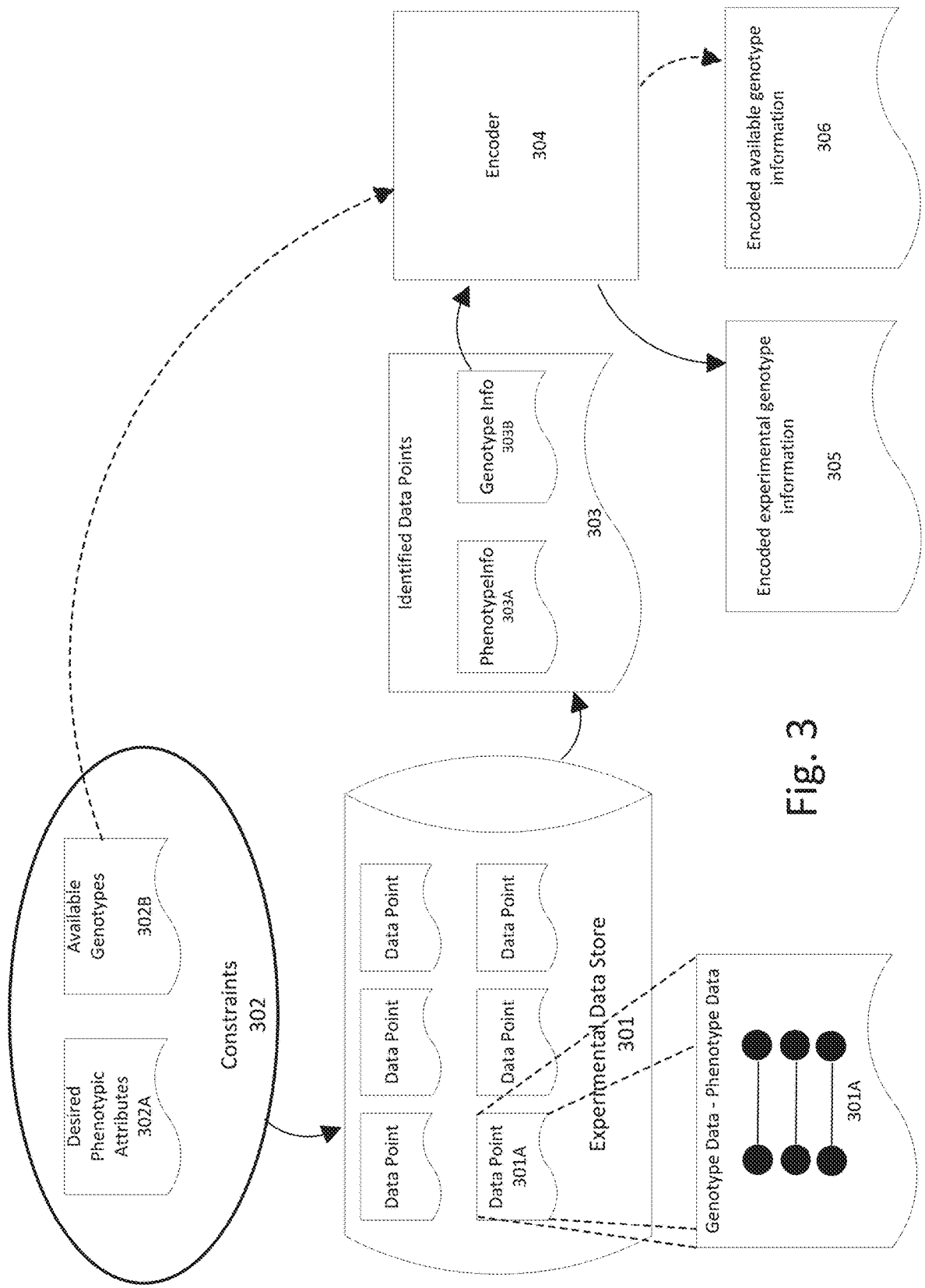
FIG. 3 illustrates a data flow chart showing the process for generating encoded representations of available genotypes and genotype information in the experimental data points according to an exemplary embodiment.

FIG. 3 illustrates a data flow chart showing the process for generating encoded representations of available genotypes and genotype information in the experimental data points according to an exemplary embodiment.

As shown in FIG. 3, constraints 302 including a plurality of desired phenotypic attributes 302A and a plurality of available genotypes 302B can be received. This receiving step can include encoding the plurality of available genotypes 302B with an encoder 304 to generate encoded available genotype information 306. This data flow is shown by the dashed arrows. As discussed previously, when using certain encoding schemes, such as embedding schemes (discussed below), the encoded available genotype information 306 can include to a plurality of available genotype vectors.

As additionally shown in FIG. 3, the constraints 302 are applied to the experimental data store 301, containing multiple experimental data points, to identify a plurality of experimental data points 303 corresponding to the constraints 302. Data point 301A illustrates an example of how genotype data can be linked to corresponding phenotype data within each experimental data point. The identified experimental data points will include genotype information 303B and phenotype information 303A corresponding to the genotype information 303B. The genotype information 303B is then supplied to the encoder 304, which encodes it to generate encoded experimental genotype information 305. As discussed previously, when using certain encoding schemes, the encoded experimental genotype information 305 can include a plurality of experiential genotype vectors 305. The different encoding techniques that can be used by the encoder are discussed in greater detail below.

Encoding DNA Parts Using Embeddings for Sequential Model Based Optimization (SBMO) Strategy As will be discussed in greater detail further below, the disclosed systems and method can be implemented using SBMO. The SMBO strategy for biological systems can be applied using different ways to represent data. The most direct way is to just use labels. With the "label representation" the gene variants and promoter sequences are represented with nominal variables, so the model is expected to learn from data how these labels are related to each other and how they affect the outcome. This kind of representation is very easy to implement and test and it doesn't need the use of the variant's genetic sequences. It just needs labels to be able to distinguish between nominal categories among the features. The drawback is that, as it can't use sequence information, the model could miss the underlying biochemical information that can be useful for the prediction task.

In order to be able to use information from DNA/Protein sequences, alternative ways to represent data can be utilized. These methods utilize Natural Language Processing and are focused on building low-dimensional numerical representations (embeddings) of text sequences. The use of a continuous numerical representation provides biological and chemical information about the variants that the learner (surrogate model) could use to make better predictions, improving the efficiency in getting an optimal design.

The building of the embeddings requires the training of machine learning models on vasts amounts of data. The number of sequences involved in the problems SMBO should apply are typically low, so the model that encodes the text information needs to be trained previously on external large datasets. This transfer learning methodology allows a model to apply knowledge from a large dataset to a more specific task.

Encoding Via Multidimensional Representation of Sequences

Through embedding techniques, sequences can be represented as vectors that lie in a multidimensional space. These vectors encode sequence information and allows making relationships in the multidimensional space that have biochemical and biophysical sense. This dense representation in a continuous space makes it possible for the model to have access to information about the sequences that allows the model to identify, extract and exploit the relationships between them.

To model biological sequences natural language processing techniques can be utilized. For this, we consider a sequence as a composition of sub units represented by symbols or sequences of symbols, which we call tokens. Each sequence is related to a set of tokens. In our case, these tokens can be defined as n-grams, where a n-gram is a sequence of n contiguous sequence elements. The parameter n can take values between 1 and the maximum length of all the sequences, where the length is measured according to the maximum amount of the smallest subunits in which it is possible to divide the sequence. For example in the case of proteins, these n-grams correspond to their (sub)sequences of n residues, and in the case of genes, correspond to their (sub)sequences of n nucleotides or codons, etc.

A parametric model, such as a neural network with one or more layers, can be utilized to learn a multidimensional representation for each token. This can be done using a representation learning algorithm (such asWord2Vec, GloVe, FastText, Autoencoders, Variational Autoencoders (VAEs), ProtVec and GeoVec, dna2vec, etc.)

The above method allows for representation of larger sequences using, for example, a weighted sum of n-grams. This weighting can be learned by a parametric model such as a neural network with one or more layers. It can also be the arithmetic sum, the average, the weighting by the inverse of the frequency of the tokens, among others. The resulting representation contains enough information, for example, to group the sequences according to their biochemical and biophysical properties.

Similar methods can be used to train Language Models that directly translate sequences into vector representations, without defining explicitly an arithmetic for combining token representations. Some of these approaches include the training of Recurrent Neural Networks on token prediction tasks or use models like Autoencoders, VAEs, BERT, etc.

When using the embedding approach, the input of the surrogate will be fully continuous. Hence, the SMBO might take advantage of this and use a surrogate model with analytical optimum (such as Gaussian Process) or derivable (such as Deep Ensembles, Deep Gaussian Processes, Bayesian Networks or other Bayesian approaches). In case of using a derivable model, optimum can be searched by means of Gradient Descent algorithm, Stochastic Gradient Descent or similar.

Returning to FIG. 1, at step 103 a phenotype prediction model is trained based at least in part on the plurality of experiential genotype vectors, the corresponding phenotype information, and the one or more constraints.

The phenotype prediction model is a surrogate model (sometimes referred to as a metamodel or a substitute model) that is used to approximate an objective function. A surrogate model is a model that approximates the behavior of a more complex model or physical system as closely as possible. Surrogate models can be utilized when the computational complexity of a physical system, experimental data points, and/or constraints would result in computationally indeterminable or infeasible training or application steps.

The prediction models and optimization techniques that can be used with the disclosed systems and methods are discussed in greater detail below.

Sequential Model Based Optimization (SMBO)

SMBO algorithms are a family of optimization methods based on the use of a predictive model to iteratively search for the optimum of an unknown function. They were originally designed for experimental design and oil exploration. SMBO methods are generally applicable to scenarios in which a user wishes to minimize some scalar-valued function $f(x)$ that is costly to evaluate. These methods progressively use the data that is compiled from a process or objective function to adjust a model (named as the surrogate model). This model is used on each iteration to make predictions of the objective function over a set of candidates, which are ranked according to their predicted score. On each iteration, the top ranked candidate is suggested to be evaluated for the next iteration.

SMBO has never been applied before to the optimization of a biological system, which poses specific challenges that are addressed by the methods, apparatuses, and computer-readable media disclosed herein.

When ranking candidates, SMBO methods usually use a scalar score that combines the predicted value with an estimation of its uncertainty for each sample. The intuition behind using the uncertainty is that the reliability of the predictions may decrease on unexplored areas of the solution space. Also, the consideration of an uncertainty term in the acquisition function promotes the exploration and the diversity of recommendations, helping to avoid local optima. There are many options for acquisition functions in literature. One of the most commonly used is the expected improvement (EI).

There can be found several SMBO methods in literature. These methods differ from the present system on the modeling approach. One of the most known methods is called Bayesian Optimization, which uses Gaussian Processes (GP) as a surrogate model. This approach has been successfully applied in many fields, however GP modeling cannot be applied directly to discrete variables (like genotypes). Other approaches include Hyperopt (or TPE algorithm) which uses a Tree-Structured Parzen Estimator and SMAC which uses Random Forests (RF) as surrogate model.

As noted before, one of the most common acquisition functions is called Expected Improvement (EI). The general formulation is:

$$EI(x)=E[f(x)-f(x^*)]$$

where $f(x^*)$ is the current optimum value and $f(x)$ is the value of the surrogate's prediction. As it is required a random variable to calculate expectancy, $f(x)$ should be associated with a probability function. Unfortunately, with most machine learning models it's not trivial to obtain a distribution of a prediction (instead of just a plain prediction value) to be used as surrogate. For this, a possible approach (among a few others) is to use Random Forests (RF). With this method, the RF prediction is used as an estimation of the statistical mean of the surrogate model's predictions, for which a gaussian distribution is assumed. The calculation of the variance of the prediction considers RF's estimators deviation and the leaf training variance for each tree. Both estimations are combined using the Law of total variance.

Classic SMBO approaches are formulated to recommend one experimental observation per iteration. However, in the context of optimizing a biological system, a single experiment can typically make multiple evaluations of the objective function. In those cases, experimental recommendations should be grouped into batches, and the method should be able to suggest on each iteration a batch of n candidates $x_1$ when $j \in \{1, \ldots, n\}$ instead of just one single recommendation.

The simplest way to recommend a batch of n experiments is to get the n optimal values from the acquisition function. However, this criterion ("take the n designs with highest acquisition values") may not consider that some designs in the selected set may be very close to each other, reducing solution's space exploration and incurring in wasteful experimental evaluations. A possible strategy to deal with batch suggestions is the use of the constant liar technique. With this technique, the first candidate, $x_1$, is obtained by maximizing the acquisition function in the same way as for the single sample case. However, to obtain $x_{j+1}$ it is assumed that the evaluation at point $x_j$ exists, and the model is retrained adding a fabricated value for $x_j$'s evaluation into the training dataset. Then, the new acquisition function is maximized to obtain the next candidate. There are several heuristic options to decide how to fabricate the latter value. Another thing to consider is that, on categorical domains, and when the surrogate can't or doesn't attain an analytical optimum, each of the constant liar steps may require a lot of computational effort (as the maximization may require the evaluation of all possible candidates).

Random Forests are models of the type ensemble that are based on grouping multiple models of low complexity. They carry this name because they use multiple Decision Trees whose prediction is averaged to obtain the final estimation of the model. Random Forests can be used for both classification and regression problems and in spaces of continuous, discrete or categorical variables.

Figure 8:
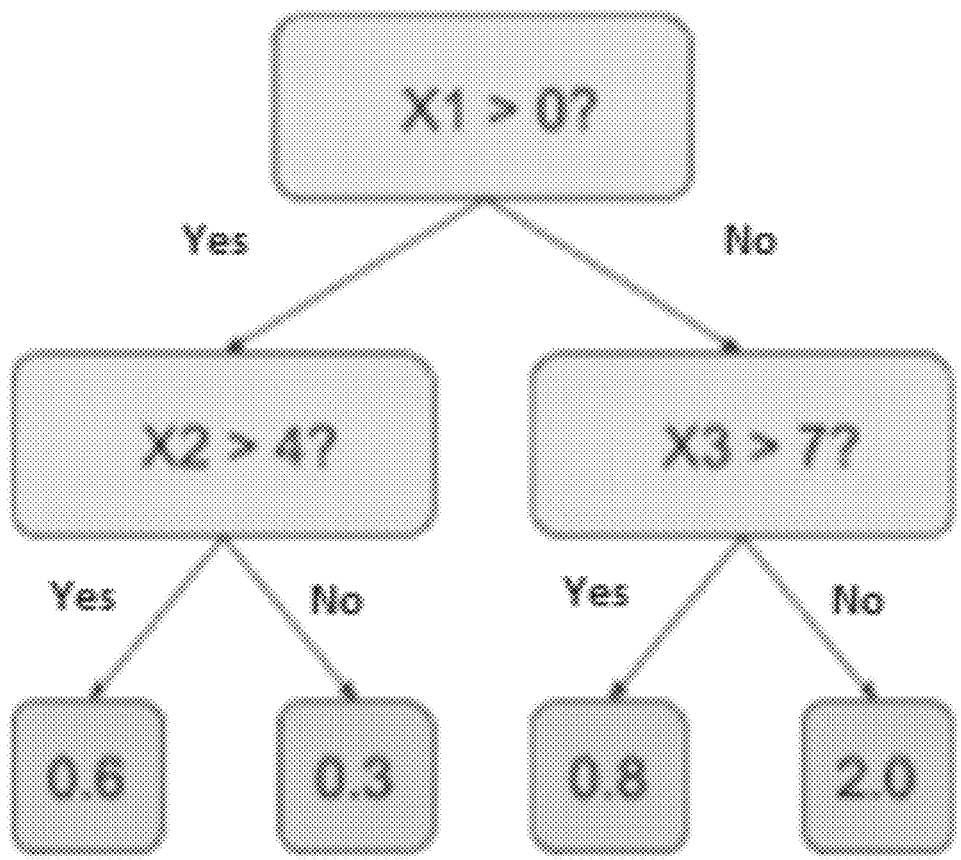
FIG. 8 illustrates an example of depth decision tree 2 used in a regression problem.

FIG. 8 illustrates an example of depth decision tree 2 used in a regression problem. In front of a certain input or sample, the decision tree classifies it gradually (from top to bottom) according to the values of its characteristics. As a prediction, the tree gives the value associated with the sheet in which said entry was classified.

With Random Forests being models of the type ensemble and considering the way in which they are trained, the overfit can be avoided by means of the appropriate choice of the configuration meta-parameters. This makes them quite useful in problems where there is not a lot of data.

Figure 4:
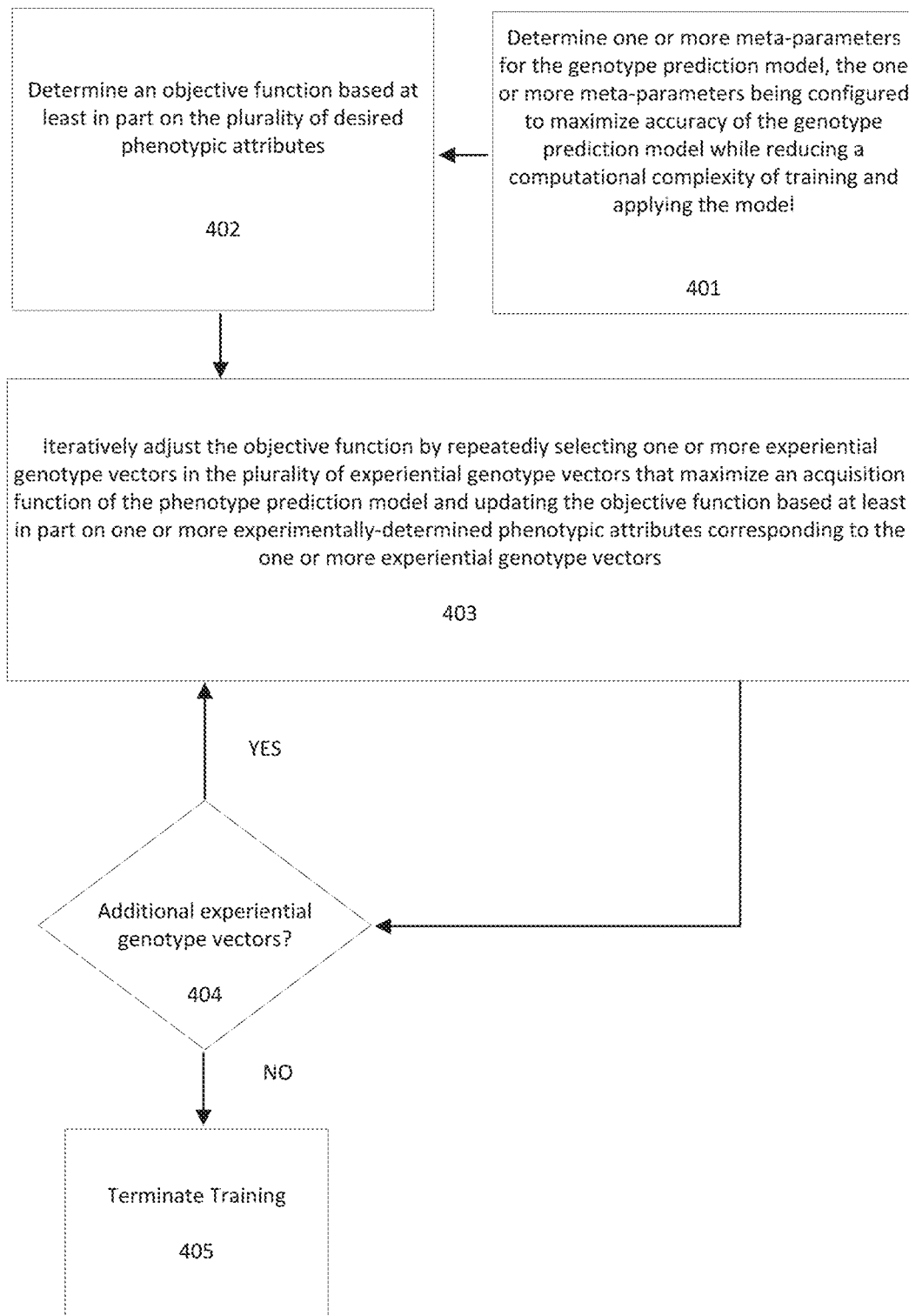
FIG. 4 illustrates a flowchart for training a phenotype prediction model based at least in part on the plurality of experiential genotype vectors, the corresponding phenotype information, and the one or more constraints according to an exemplary embodiment.

FIG. 4 illustrates a flowchart for training a phenotype prediction model based at least in part on the plurality of experiential genotype vectors, the corresponding phenotype information, and the one or more constraints according to an exemplary embodiment.

At step 401 one or more meta-parameters are determined for the surrogate model, the one or more meta-parameters being configured to maximize accuracy of the surrogate model while reducing a computational complexity of training and applying the model. This step is discussed in greater detail below.

Selection of Meta-Parameters for Random Forests

An important problem when implementing the disclosed scheme is to find the appropriate meta-parameters for the surrogate model to be used.

In a concrete use case, approximately 140 experimental observations are available. This could be considered a very small sample considering that the search space is more than 140,000 designs of 6 categorical dimensions (translated, in scheme variable dummy, to about 80 binary dimensions). These characteristics imply the carrying out of a meticulous analysis to define the architecture of the model to be used.

Figure 9:
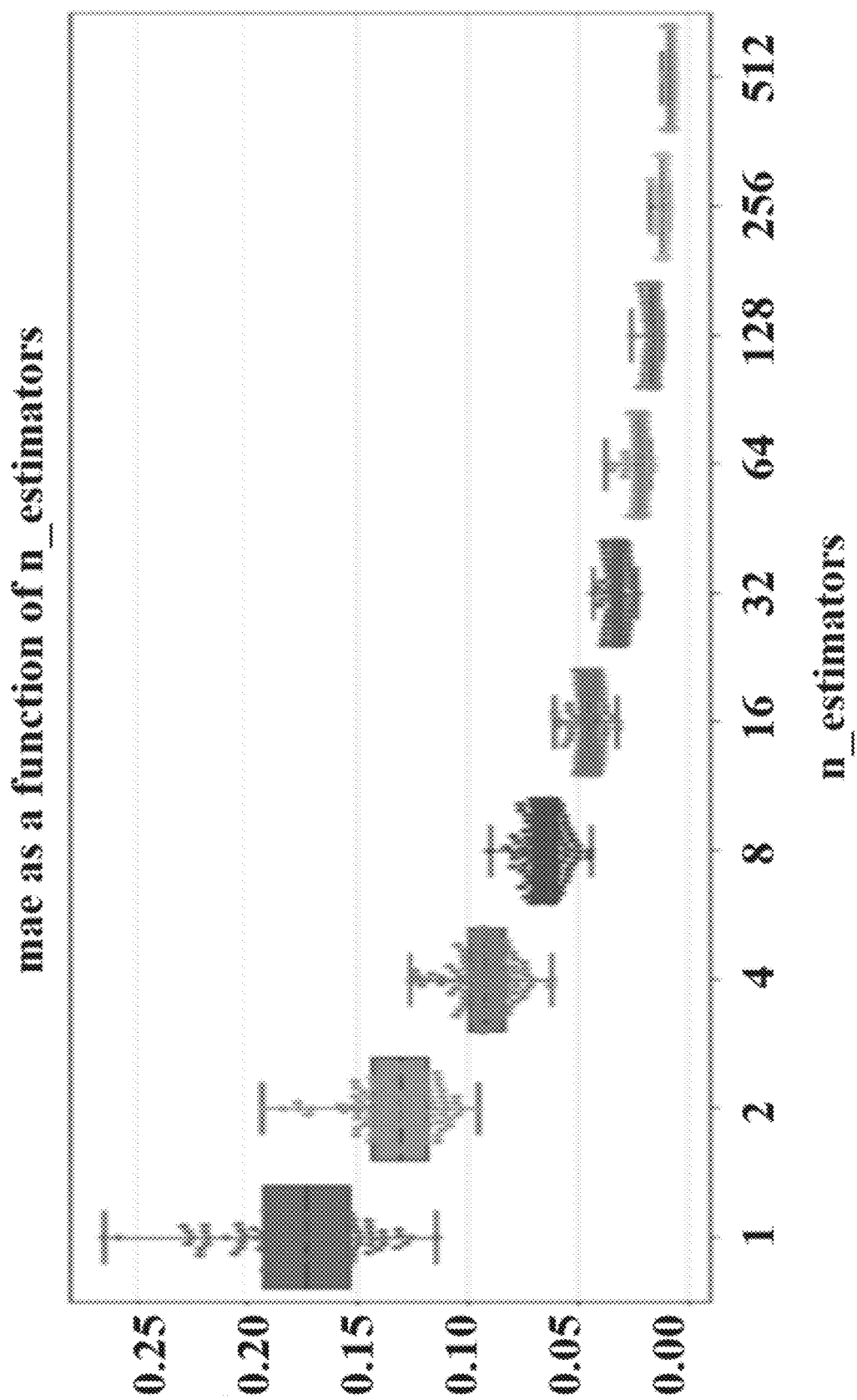
FIG. 9 illustrates an experimental analysis carried out to determine which value of number of estimators maximizes the accuracy and repeatability of the prediction.

For Random Forests, some of the most important meta-parameters are the number of estimators, which corresponds to the number of binary decision trees that make up the model, and the maximum depth, which defines the maximum height allowed for each of the trees. Different values of these meta-parameters can generate very different results. For their search, multiple cross-validation experiments were carried out, generating independent models in different sets of training and test data. FIG. 9 illustrates part of this work, where the influence of the parameter was studied number of estimators on the model's accuracy.

In particular, FIG. 9 illustrates an experimental analysis carried out to determine which value of number of estimators (n_estimators) maximizes the accuracy and repeatability of the prediction. For each value of n_estimators (each value in different column), with experimental data, 100 models were trained and used to predict the production level of a set of hypothetical designs (1e, without experimental data). Then, the average estimate of the set was calculated and the Mean Average Error (MAE) of each individual model was evaluated with respect to this average (points). This was done for different values of the number of estimators and the distribution of the errors expressed in quartiles was added to the graph. From this scheme it is possible to infer that for the experimental conditions, the accuracy of the model improves as the number of estimators increases. In other words, results of independent trainings of the model are more repeatable to a greater number of estimators.

Once the parameters that define the architecture of the model have been found, the SMBO logic can be applied to determine the next points to evaluate experimentally and to successively update the predictive model until the most optimal phenotype has been determined.

Returning to FIG. 4, at step 402 an objective function is determined based at least in part on the plurality of desired phenotypic attributes. The process of recommending genotypes for experimentation involves maximization of the objective function, as well as maximization of an acquisition function and additional steps, as discussed in greater detail further below.

At step 403 the objective function is iteratively adjusted by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors. As discussed elsewhere in this specification, this can be performed by modeling the plurality of experiential genotype vectors as a random forest and training the random forest using the corresponding experimentally-determined phenotypic attributes.

The process of step 403 is repeated until all of the experiential genotype vectors in the plurality of experiential genotype vectors are processed. Specifically, at step 404 a determination is made regarding whether there are additional experiential genotype vectors in the plurality of experiential genotype vectors that have not yet been processed. If so, then step 403 repeats. Otherwise, the training is terminated at step 405.

Returning to FIG. 1, at step 104 the phenotype prediction model is applied to a plurality of available genotypes corresponding to the set of constrains to generate a plurality of scores, the phenotype prediction model being configured to predict one or more phenotypic attributes of the plurality of available genotypes.

This step can include applying the objective function to the plurality of available genotype vectors to generate a plurality of prediction scores corresponding to the plurality of available genotype vectors. This step can also include applying an acquisition function of the phenotype prediction model to the plurality of available genotype vectors to generate a plurality of acquisition scores corresponding to the plurality of available genotype vectors. Additionally, this step can include determining an uncertainty score associated with available genotype vector in the plurality of available genotype vectors.

At step 105 a plurality of result genotypes are determined based at least in part on a ranking of the plurality of available genotypes according to the plurality of scores. This step can include ranking the plurality of available genotype vectors based at least in part on the plurality of prediction scores corresponding to the plurality of available genotype vectors and filtering out a percentage of the plurality of available genotype vectors below a predetermined ranking percentage to generate a plurality of result genotype vectors. The predetermined ranking percentage can be set by a user, set to some default value, based upon prior results or the particulars of the constraints or the experimental data set, or based upon implementation details of the particular predictive model type utilized.

At step 106 a result is generated based at least in part on the plurality of result genotypes, the result indicating one or more genetic constructs for testing. As discussed in greater detail below, this result can be a batch of single genetic constructs for testing or a combinatorial sequence that specifies multiple genetic constructs for testing. A user can optionally select whether they wish to receive a list of single genetic constructs or a combinatorial sequence.

Construct is used as a synonym of "candidate." Each construct represents a particular combination of genotype variants. For example, a combinatorial DNA design of complexity N, will lead to the assembly of N constructs.

The step of generating a result can include ranking the plurality of result genotype vectors based at least in part on an acquisition score associated with each result genotype vector and selecting one or more result genotype vectors in the plurality of result genotype vectors based at least in part on the ranking. This step can further include decoding the result genotype vectors to present the genotype information in a format that the user can understand and utilize or create in an experimental setting.

This step can be configured to select only the top-ranked result genotype vector. However, in the scenario where a user has specified that they would like a batch of results (genetic constructs for testing), the system must determine whether sufficient constructs have been generated and otherwise take the appropriate actions to update the model and generate additional constructs.

Figure 5:
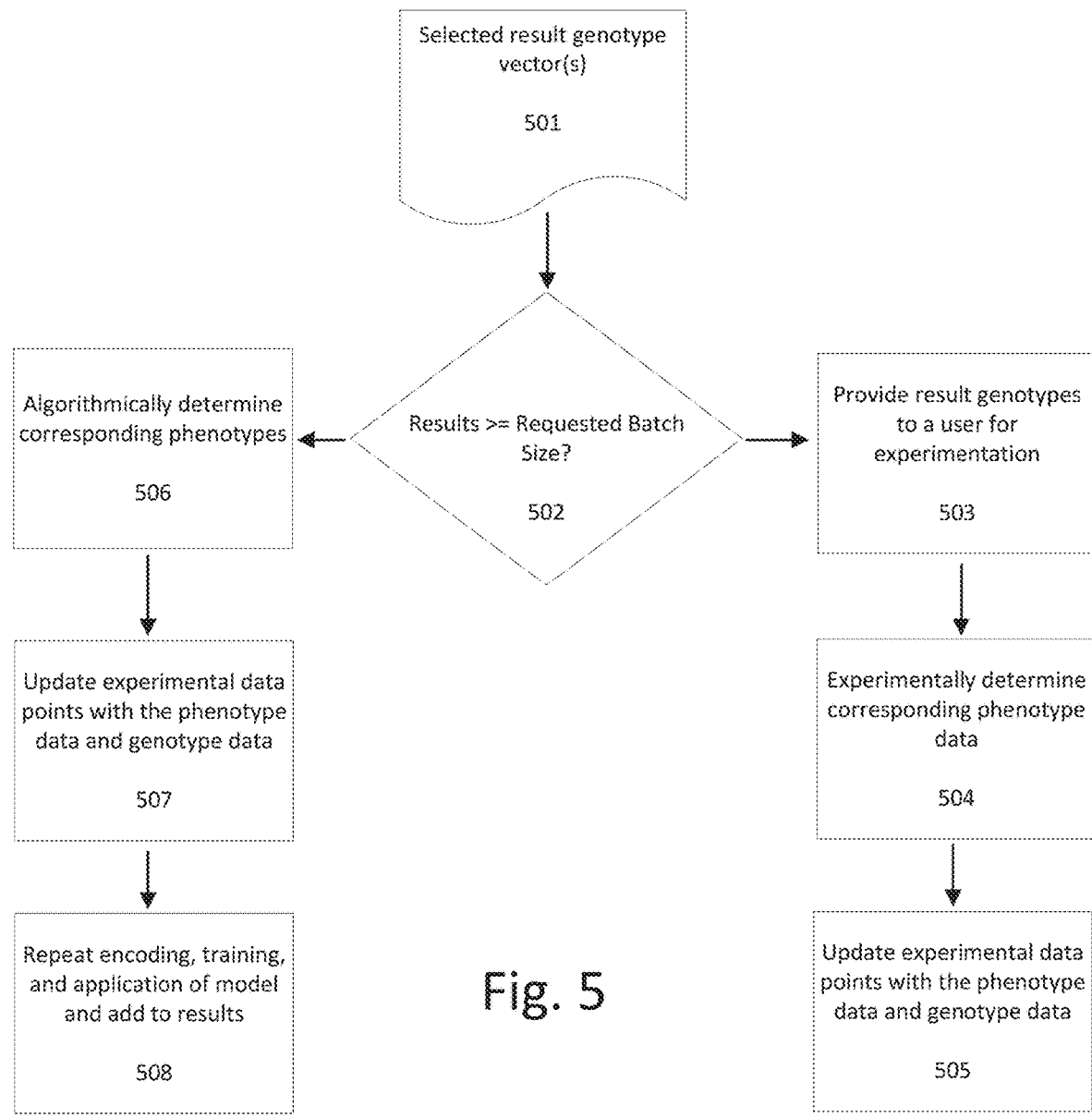
FIG. 5 illustrates a flowchart for updating the predictive model and determining whether to generate additional constructs according to an exemplary embodiment.

FIG. 5 illustrates a flowchart for updating the predictive model and determining whether to generate additional constructs according to an exemplary embodiment. As shown in FIG. 5, one or more selected result genotype vectors are the output of an initial application (evaluation) of the predictive model. At step 502 it is determined whether the quantity of results is greater than or equal to the requested batch size.

If so, then at step 503 the result genotypes corresponding to the selected result genotype vectors are provided to a user, at step 504 the user experimentally determines phenotype data (phenotype measurements) corresponding to the result genotypes, and at step 505 the experimental data points are updated with the genotype data of the results and the corresponding phenotype data.

If at step 502 the results are determined to be less than the requested batch size, then the process proceeds to step 506. At step 506 phenotypes corresponding to the selected result genotype vector are algorithmically generated. These generated phenotypes are fabricated values and can be generated in a variety of ways. One way to generate these phenotypes is use a phenotype prediction generated by the phenotype prediction model. Another way is to use the phenotype prediction minus the standard deviation of the prediction. Yet another way is to use some other linear combination of the predicted phenotype and its corresponding standard deviation. After the phenotypes are generated, the experimental data points are updated with the genotype data of the results and the corresponding phenotype data at step 507.

At step 508, the steps shown in FIG. 1 of encoding genotype information in the experimental data points, training the model, applying the model, determining result genotypes, and generating a result are repeated with the updated experimental data points. This includes encoding genotype information in the updated plurality of experimental data points corresponding to the set of constraints as an updated plurality of experiential genotype vectors, retraining the phenotype prediction model based at least in part on the updated plurality of experiential genotype vectors, the corresponding phenotype information, and the one or more constraints, applying the phenotype prediction model to remaining available genotypes in the plurality of available genotypes corresponding to the set of constrains to generate an updated plurality of scores, determining an updated plurality of result genotypes based at least in part on an updated ranking of the remaining available genotypes according to the updated plurality of scores, and generating an additional result based at least in part on the updated plurality of result genotypes, the additional result indicating one or more additional genetic constructs for testing.

As shown in FIG. 5, regardless of whether the results are less than the requested batch size or greater than or equal to the requested batch size, a determination of phenotype data corresponding to the selected one or more result genotype vectors is made and the plurality of experimental data points are updated with the phenotype data and genotype data corresponding to the selected one or more result genotype vectors.

As discussed above, when a user requests a batch of single genetic constructs for testing, the predictive model can be applied to generate either one result genetic construct at a time or multiple genetic constructs per iteration. When multiple genetic constructs are determined per iteration, Applicant has discovered optimizations which reduce noise and improve computational efficiency. These optimizations are discussed in greater detail below.

Recommending Multiple Experiments (n_Batch Experiments)

In order to recommend a set of N candidates simultaneously, the optimization framework should provide several candidates per iteration step. For this, the disclosed method repeats the training and evaluation steps as much as needed, following the constant liar method. The actual predicted value of the untested candidate was used as fabricated value.

When maximizing the acquisition function within the liar approach, considering that usually the problem is restricted to a fixed number of possible designs, the most accurate way to find the optimal candidate is to evaluate the acquisition function in all designs. The drawback of this approach is that the number of possible designs could be huge, implying large computation times. This problem can be overcome by randomly sampling a fixed number of designs (10.000) from all possible designs for evaluation and selection of the optimal. However, this implementation may introduce an inconvenient noise factor into the formulation, making difficult to achieve consistent predictions between models trained with the same data. To speed up the algorithm without compromising accuracy, the applicants introduced a new heuristic rule: Instead of evaluating all possible designs or making a random subset of all candidates, a subset is built from the a % candidates with top predicted values. This limits the calculation time and ensures more consistency between different runs. The idea is to identify $\alpha$ that can define a list of top prediction candidates that will probably contain all selected candidates from the liar approach. We found that a value of a set to 60% worked on most of the experiments that we run. It should be noted that $\alpha$ value may change if a different number of selected candidates is required (we've set the limit to 100 candidates by default, as clients are rarely interested in having more). The use of the a rule helps to cut down by near a half the computation time without adding unnecessary randomness to the batch generation process.

FIG. 5 described the scenario where a user requested a batch single genetic constructs. However, a user can also specify that the step of generating a result should return a combinatorial design that is used to generate multiple genetic constructs.

Figure 6:
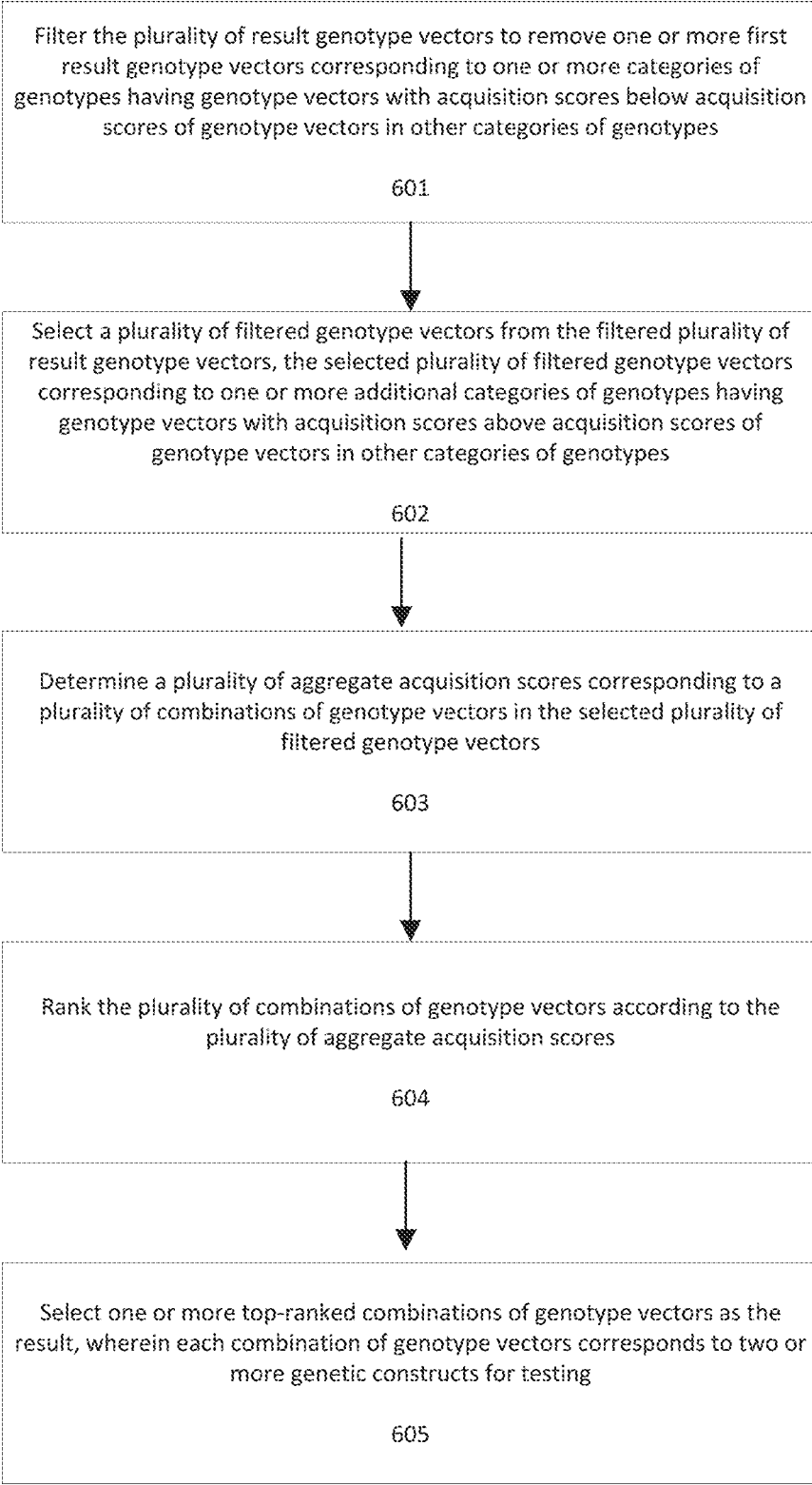
FIG. 6 illustrates a flowchart for generating a result based at least in part on the plurality of result genotypes when the user requests a combinatorial design according to an exemplary embodiment.

FIG. 6 illustrates a flowchart for generating a result based at least in part on the plurality of result genotypes when the user requests a combinatorial design according to an exemplary embodiment.

At step 601 the plurality of result genotype vectors are filtered to remove one or more first result genotype vectors corresponding to one or more categories of genotypes having genotype vectors with acquisition scores below acquisition scores of genotype vectors in other categories of genotypes.

The word "category" is used herein as a synonym of genotype variant. For example, if each gene included in a design contains only one category (genotype variant), then the design would not be considered "combinatorial."

At step 602 a plurality of filtered genotype vectors are selected from the filtered plurality of result genotype vectors, the selected plurality of filtered genotype vectors corresponding to one or more additional categories of genotypes having genotype vectors with acquisition scores above acquisition scores of genotype vectors in other categories of genotypes.

At step 603 a plurality of aggregate acquisition scores are determined corresponding to a plurality of combinations of genotype vectors in the selected plurality of filtered genotype vectors.

At step 605 the plurality of combinations of genotype vectors are ranked according to the plurality of aggregate acquisition scores.

Additionally, at step 606 one or more top-ranked combinations of genotype vectors are selected as the result, each combination of genotype vectors corresponding to two or more genetic constructs for testing.

The process for generating a result based at least in part on the plurality of result genotypes when the user requests a combinatorial design corresponding to steps 601-606 is explained in greater detail below, with reference to specific examples.

Recommending Combinatorial Output

Applicant has developed a method for returning a reduced combinatorial design as output (instead of recommending a linear list of constructs). This can streamline the process of genotype optimization. The present section describes in detail a novel method to find the optimal combinatorial design out of the predictions over all single candidates.

When optimizing an organism by means of synthetic biology, some of the most common problems look as follows:

| Gene 1 | Gene 2 |
|---|---|
| Gene_1_variant_1 | Gene_2_variant_1 |
| Gene_1_variant_2 | Gene_2_variant_2 |
|  | Gene_2_variant_3 |

Table 1 illustrates an example of a combinatorial design. It contains 2 genes and each gene has a different number of possible variants. This specific example represents a biochemical reaction that depends on two enzymes of different kinds. Those enzymes are encoded as genes. The scientist has found 2 valid sequence alternatives for the first enzyme, and 3 options for the second gene.

Usually there is a set of bins or positions in a genetic design where, within each bin, there's a limited number of possibilities to choose from. In the example case, the first gene position or bin may have 1 from 2 different alternatives, while the second gene has 3 variants to choose from.

The data displayed at table 1 represents a combinatorial design. Usually the scientist is searching for the best combination of the variants and looks for the one with the highest production rate of a certain product. Given the above example, there are 6 possible solutions for the problem which are generated from the combinations of all variants. In the following table, each row represents one of these, also called as "single solutions" or constructs:

| Construct ID | Gene 1 | Gene 2 |
|---|---|---|
| 1 | Gene_1_variant_1 | Gene_2_variant_1 |
| 2 | Gene_1_variant_1 | Gene_2_variant_2 |
| 3 | Gene_1_variant_1 | Gene_2_variant_3 |
| 4 | Gene_1_variant_2 | Gene_2_variant_1 |
| 5 | Gene_1_variant_2 | Gene_2_variant_2 |
| 6 | Gene_1_variant_2 | Gene_2_variant_3 |

Table 2 illustrates a list of the 6 singular solutions/constructs associated with the combinatorial example shown in Table 1.

As it was noted before, the scientist is looking for a construct within a combinatorial design that maximizes a specific experimental measurement. This is the kind of candidate solution that SMBO methods provide. Single solutions. In this case, the scientist should build each of the proposed candidates, make experiments, evaluate them in the lab, feed the algorithm and continue with the DBTL cycle until criteria is met. This process works fine, however there is room for improvement.

One of the shortcuts that biochemistry allows scientists to do is to generate all of the constructs from a combinatorial design at once, with just a few biochemical reactions. This is not free, as sequencing and labelling all combinations from a huge combinatorial design can be very hard, but the applicants have found that in some cases the algorithm can take advantage of this property and streamline the optimization process.

As scientists can find interesting to work with combinatorial designs of limited complexity (instead of working with a huge combinatorial design or lists of isolated constructs) the Combinatorial Solution option was implemented to suggest a "reduced" combinatorial design rather than a list of single candidates. This approach can allow the user to test hundreds or thousands of different meaningful designs at each optimization step, instead of just a few. Depending on the nature of the problem, this kind of solution may reduce experimental costs, hence increasing the number of samples tested on each iteration and improving the achieved optima. Also it may help to reduce experimentation time.

The Combinatorial Output is a new step in the optimization process that runs (optionally) after all single candidates are evaluated. Considering that part of this method can be computationally demanding, the applicants created a first filtering stage, where some categories are discarded by using some heuristic rules, and then a fine-tuning stage where all the remaining categories are studied in detail.

The first stage uses two pre-filter methods. The first one finds, for each bin the worst performing categories where all its singular construct's scores are below the ones of the other categories. After identifying these low scored categories, the associated singular constructs are removed from the candidates list. Then, the second pre-filter is applied, which starts building a combinatorial design by collecting the best top 'N' performing categories according to a ranking based on the acquisition value of their corresponding singular candidates. The number 'N' of collected categories will be given by a pre-determined combinatorial complexity threshold. The combinatorial complexity is given by the product formula below. Where $n_{bi}$ and $n_{bf}$ correspond, respectively, to the initial number of categories and the final number of categories of bin 'b'. The final number of categories of each bin is pre-determined by the user based on her needs.

$$\text{Combinatorial Complexity} = \prod_{b=1}^{|b|} (n_{bi} \text{ choose } n_{bf})$$

Higher combinatorial complexity means wider exploration space, increasing the chances of attaining global optima, but at the cost of a higher computational complexity. The result of the first stage will then be another combinatorial design, with lower complexity (due to the pre-filtering), that will be used as the input for the second stage.

The second stage (fine-tuning) is an exhaustive search that calculates a score for all possible combinatorial candidates of limited complexity that can be derived from the input combinatorial design (the one coming from the first stage). The implementation of this method is not trivial as complexity scales quickly with the size of the input and resources should be managed carefully. In what follows from this section, in addition to describing in detail the strategy approached to find the optimum, the limitations of the algorithm are studied. The latter allow to define the combinatorial complexity threshold to be used in the filtering stage.

The fine-tuning stage basically calculates an aggregated score from the acquisition values of every single construct that belongs to each combinatorial candidate. The user may select the score to be the average acquisition value of the constructs, or the maximum, or in fact, any other combination of the statistics of the acquisition values (s.a: mean, standard deviation). Based on this score, the best combinatorial designs are stored during execution and returned to the user after evaluating all combinatorial candidates.

To better understand what the fine-tuning stage does, consider the acquisition function results of the constructs from the previous example:

| Construct ID | Gene 1 | Gene 2 | Acquisition score |
|---|---|---|---|
| 1 | Gene_1_variant_1 | Gene_2_variant_1 | 2.12 |
| 2 | Gene_1_variant_1 | Gene_2_variant_2 | 3.01 |
| 3 | Gene_1_variant_1 | Gene_2_variant_3 | 4.02 |
| 4 | Gene_1_variant_2 | Gene_2_variant_1 | 3.11 |
| 5 | Gene_1_variant_2 | Gene_2_variant_2 | 3.98 |
| 6 | Gene_1_variant_2 | Gene_2_variant_3 | 5.03 |

Table 3 illustrates acquisition values for each construct within a hypothetical (big) combinatorial design. Acquisition values will be combined to calculate the scores for each (reduced) combinatorial candidate.

Depending on the requirements, the user can set the final desired complexity or, alternatively, the maximum number of categories per bin of the output combinatorial design. This will determine the number of possible different constructs that can be derived from the resulting combinatorial design and, also, define the set of all combinatorial candidates to be ranked. For instance, following our example case, if the scientists wants a combinatorial output with $n_f=2$ final categories per bin, the number of constructs that can result from that output is $s_f=(n_f)^b=4$, and the resulting candidates will be the ones listed in the following table. This table also shows the calculation of candidates' scores:

| Combinatorial Design ID | Gene 1 | Gene 2 | Single constructs ID | Aggregated Score (average) |
|---|---|---|---|---|
| 1 | Gene_1_variant_1 Gene_1_variant_2 | Gene_2_variant_1 Gene_2_variant_2 | 1, 2, 4, 5 | 3.06 |
| 2 | Gene_1_variant_1 Gene_1_variant_2 | Gene_2_variant_1 Gene_2_variant_3 | 1, 3, 4, 6 | 3.57 |
| 3 | Gene_1_variant_1 Gene_1_variant_2 | Gene_2_variant_2 Gene_2_variant_3 | 2, 3, 5, 6 | 4.01 |

Table 4 illustrates combinatorial candidates for the example problem with their respective scores.

The Combinatorial Solution method returns the top ranked combinatorial designs according with the aggregated scores. The user may build all the associated constructs from one or more proposed solutions and evaluate them. After that, she can feed the model with constructs' data and generate a new set of combinatorial or singular candidates.

From the example above, this problem (scoring all combinatorial candidates) seems very simple. However, the number of combinatorial candidates explodes with big combinatorial designs so, from the computational complexity perspective, the implementation of this solution provides many challenges.

A typical strain optimization problem contains b=6 bins and a number of original categories per feature $n_o=7$. The number of all single solutions will be given by the expression:

$$s=(n_0)^b$$

which here takes the value s=117,649.

If the user wants to reduce to $n_f=2$ final categories per feature, the number of combinatorial candidates will be given by the following expression:

$$c=(n_0 \text{ choose } n_f)^b$$

which in this case takes the value c=85,766,121 combinatorial candidates (and increases quickly with bigger values of $n_o$)

One way to achieve massive calculations these days is by using graphical processing units (GPUs) to take advantage of their parallel processing capabilities. To do so is important to find a valid representation of the problem that suits the available tools to exploit hardware's parallelism. With that objective, the following definitions were made:

$S \in B^{s \times k}$: Is the binary matrix of single solutions. Each row represents a single solution and each column represents one of k total categories. Each component will have a value of 1 if the category is present in the construct and 0 if not.

$T \in R^s$: Is the target vector. It contains the float valued scores predicted for each single design.

$C \in B^{c \times k}$: is the binary matrix of valid combinatorial solutions. Each row represents a combinatorial design and each column represents one of k total categories. Each component will have a value of 1 if the category is present in the design and 0 if not.

Considering that when a single construct is contained by a combinatorial design they will share components with value "1" in b (number of bins) dimensions, we can define the Membership matrix $M \in B^{c \times s}$ as:

$$M_{i,j} = \begin{cases} 1 & (C \cdot S^T)_{i,j} \geq b \\ 0 & \sim \end{cases}$$

that will be valued "1" in position i,j iff the construct j can be obtained from the combinatorial design i.

After constructing the Membership matrix M, the single scores associated with each combinatorial design can be obtained by means of boolean indexing in the target vector T. With those acquisition values, the combinatorial aggregated score can be easily calculated.

A more formal expression for the average acquisition score specifically, denoted as the vector $A \in R^c$ for all combinatorial candidates is given by:

$$A = \frac{1}{c_f} M \cdot T$$

where $c_f$ is the number of singular constructs associated with a combinatorial candidate. This value is equal across all valid combinatorial candidates as they were selected to have the same complexity.

The above formulation was implemented for GPU execution. It has to be run in batches, as the calculations may not fit in the processor's memory. Scores are calculated using partitions $\underline{C} \in B^{bs \times k}$ of combinatorial candidates, where bs is the batch size. The best scored designs are stored during the process. The following table shows the execution times of the search of best scores, given the list of scores for the singular constructs (tests were run on an AWS p2.xlarge machine instance):

| $n_0$ | b | Number of singular candidates s | Number of reduced combinatorial samples c ($n_f = 2$) | time [h] | Batch size used (bs) |
|---|---|---|---|---|---|
| 3 | 6 | 729 | 729 | 0 | 4096 |
| 4 | 6 | 4096 | 46656 | 0 | 4096 |
| 5 | 6 | 15625 | 1000000 | 0 | 4096 |
| 6 | 6 | 46656 | 1.1E+07 | 0.2 | 4096 |
| 7 | 6 | 117649 | 8.6E+07 | 2.3 | 2048 |

Table 5 illustrates computation times of the combinatorial solution step. Results are shown for different number of categories per bin of the original combinatorial design $n_o$.

As shown on Table 5, for high values of c, calculations can become very time consuming. Also, matrix S increases its size with $n_o$, which may become high enough to not fit into memory. For this reason, the reach of the fine-tuning stage has to be limited to available resources. Using table 5, the applicants set the combinatorial complexity threshold to 8.6E+07, considering the machines that are currently available in their environment, and the amount of time their users are willing to spend on this calculation.

As explained in the above sections, Applicant has discovered a method for generating and adjusting a predictive model for optimizing the phenotype of a biological system, utilizing, for example, SMBO with a predictive model (such as Random Forests) as a surrogate that is used to estimate the outcome of untested genotypes.

Figure 7:
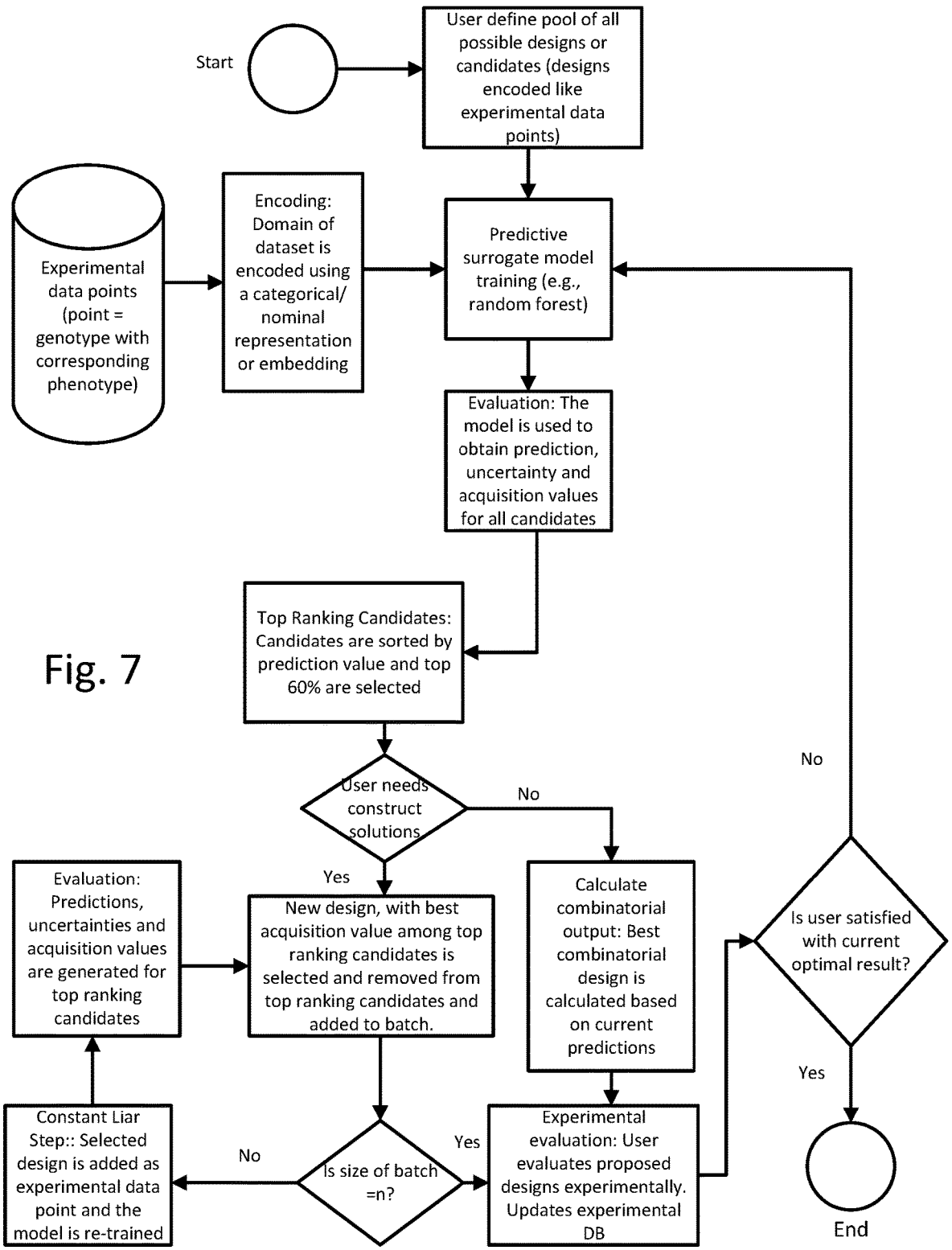
FIG. 7 illustrates high-level flowchart of the methods and system components described herein according to an exemplary embodiment.

FIG. 7 illustrates high-level flowchart of the methods and system components described herein according to an exemplary embodiment. The methods and systems described herein have many useful applications. In certain problems, bacteria are used for the production of certain high-value molecules whose production can be regulated by the insertion of metabolic enzymes encoded within donor plasmid. The efficiency of the process depends on the enzymatic variants chosen for each of the parts that make up this plasmid, so the search spaces can easily contain 100,000 genetic designs or more. This problem can hardly be solved analytically since the level of production will depend on the functioning of the complex network of metabolic circuits of the cell in interaction with the inserted agents.

In this way, given an initial set of designs evaluated in the laboratory, to find the optimal organism, a scientist may use the disclosed method and carry out an optimization process assisted by SMBO, which suggests new specific designs for its evaluation as the user is performing experimental observations.

Some of the properties of this method are:
Guides optimum search, suggesting the next experimental rounds.
Works with small datasets.
Deals with different domain spaces: Features can be categorical, numerical or mixed.
Makes predictions over untested data.
Generates reproducible results: Different runs of the algorithm outputs similar candidates.
User may ask for one or more candidates per optimization step.

The disclosed SMBO method may use as surrogate any machine/deep learning model that can manage numerical and categorical inputs, and can be configured to output an estimation of uncertainty as well as a prediction value. This includes most of ensemble-based algorithms. For example, Random Forests, XGBoost and others; also, Bayesian approaches can be used, like Bayesian Networks, etc. Additionally, includes methods based on Deep Ensembles, Bayesian Deep Learning, etc. For example, an implementation can use a sklearn implementation of Random Forest Regressor (RF) as the surrogate model.

The disclosed methods can use many different acquisition methods as scoring functions. The Expected Improvement was selected for the current implementation. However, the disclosed method is not limited to it, and any other score that can be used within the disclosed SMBO framework could also be applied.

Each single SMBO iteration of the disclosed approach considers the following steps:
Training: The surrogate model is trained on the task of predicting the experimental numeric target from the provided dataset.
Evaluation of candidates: Acquisition function value is calculated for each untested combination. Then, the results are used to rank the candidates.
Choose output type: a) or b):
 a) "combinatorial" output: If this option is considered, the algorithm looks for the best reduced combinatorial design and returns it, terminating the iteration execution (see "recommending combinatorial output" below)
 b) "list-layout" output:
  b1) Selection of best candidate: The top scored construct from step 2 is selected.
  b2) Multiple candidates: If more than 1 candidate is needed, multiple candidates are selected using the method described for recommending multiple experiments
Return all Selected Candidates SMBO Implementation In order to test the disclosed methodology, our algorithm generates a set with the next N designs (where N>=1) to be evaluated according to the criteria established by the SMBO strategy, ordered according to the level of production estimated by the predictor. This requirement involved the research of various libraries and the development of a set of tools that would allow the problem to be correctly represented. Additionally, we worked on the implementation of synthetic problems, of a known solution, to validate both the strategy and its implementation.

Figure 10:
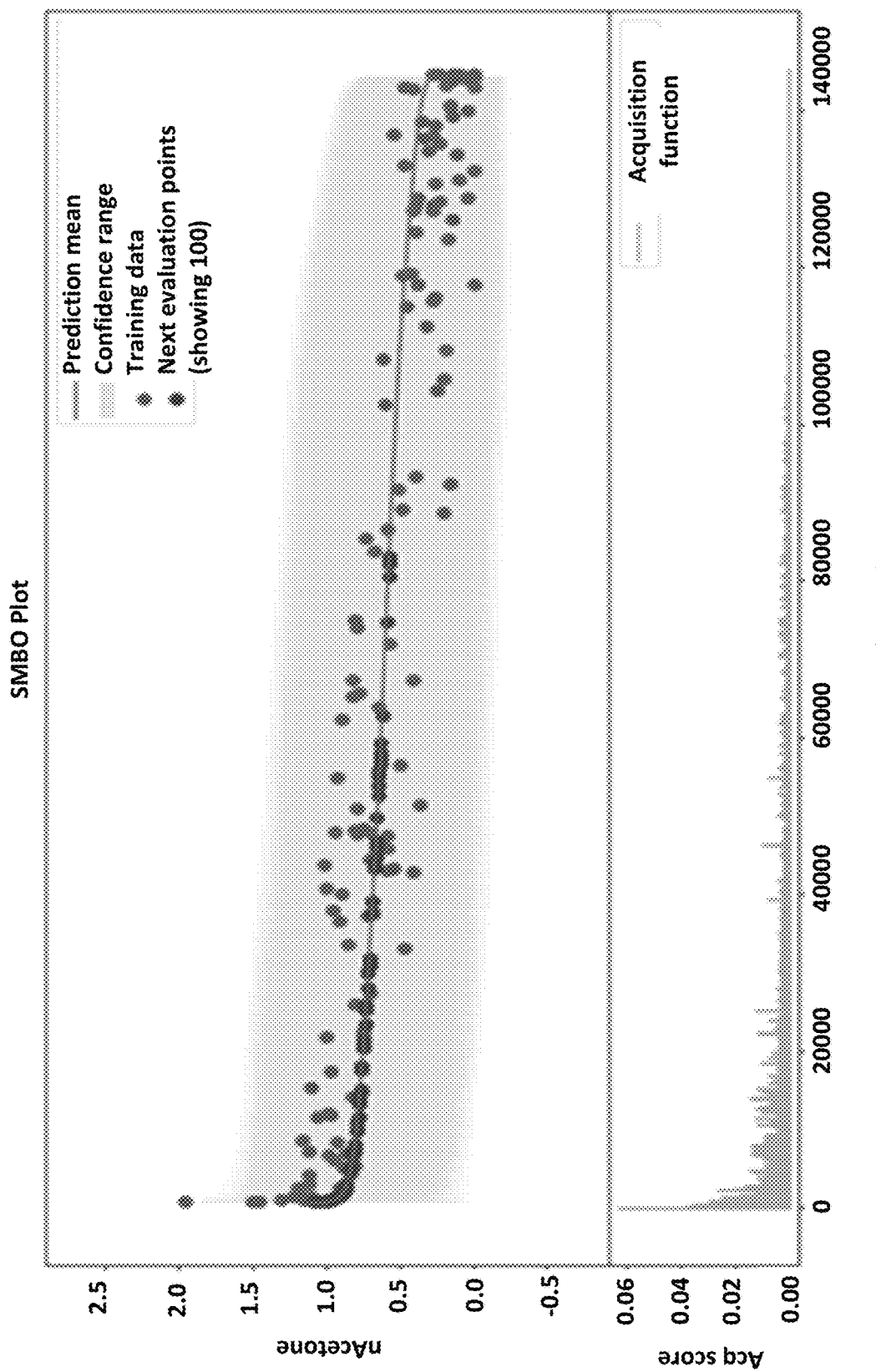
FIG. 10 illustrates the state of the SMBO optimization process at the moment of suggesting a set of new points (red) to evaluate experimentally according to an exemplary embodiment.

FIG. 10 illustrates the global SMBO graph, which shows the most important elements of the procedure performed to find the suggested data points (suggested compounds based upon the predictive model) according to an exemplary embodiment. The set of suggested points are then evaluated and used to define the next experiments that, once recorded, are used to repeat the procedure and suggest a new set of observations.

In particular, FIG. 10 illustrates the state of the SMBO optimization process at the moment of suggesting a set of new points (red) to evaluate experimentally. It shows how the selected points are distributed for their experimental evaluation according to the value of the prediction and the acquisition function. The abscissa axis represents the different possible genetic designs, which have been ordered from highest to lowest according to the prediction value of the model. In the upper graph, the axis of the ordinates represents the production rate of the molecule of interest. The prediction of the model for each possible design is represented by the blue line, while the uncertainty has been drawn as a confidence interval (celestial area) around the center of the prediction and demarcates the area where the experimental value should be found with a 95% probability. The experimental values used to carry out the modeling are shown in green. In the lower graphic it is possible to see the value of the acquisition function for each design.

Figure 11:
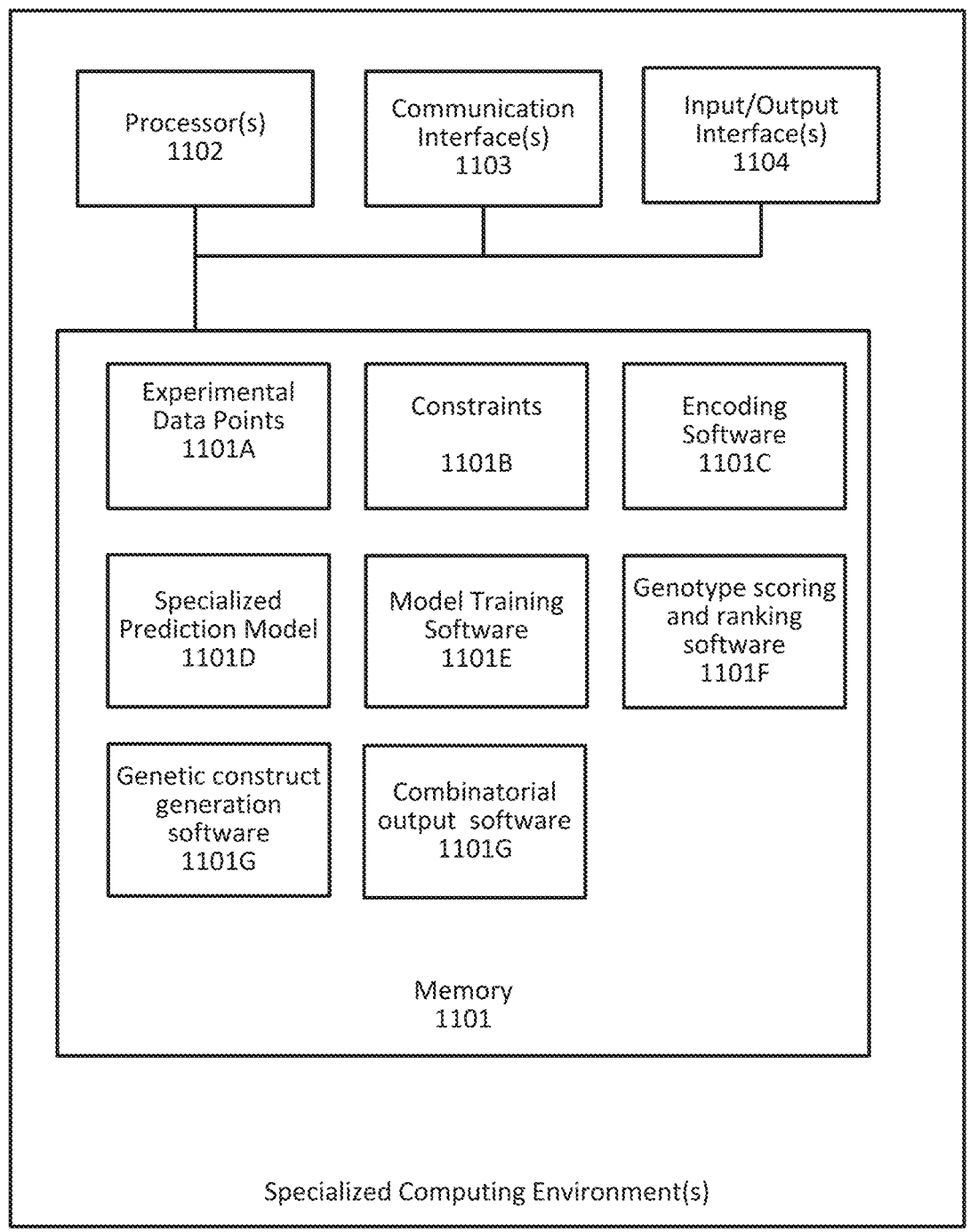
FIG. 11 illustrates the components of a specialized computing environment for efficiently optimizing a phenotype with a specialized prediction model.

FIG. 11 illustrates the components of the specialized computing environment 1300 for efficiently optimizing a phenotype with a specialized prediction model. Specialized computing environment 1100 can be made up of one or more computing devices that include a memory 1101 that is a non-transitory computer-readable medium and can be volatile memory (e.g., registers, cache, RAM), non-volatile memory (e.g., ROM, EEPROM, flash memory, etc.), or some combination of the two.

As shown in FIG. 11, memory 1101 stores experimental data points 1101A, constraints 1101B, encoding software 1101C, specialized prediction model 1101D, model training software 1101E, genotype scoring and ranking software 1101F, genetic construct generation software 1101G, and combinatorial output software.

Each of the software components in memory 1101 store specialized instructions and data structures configured to perform the methods of efficiently optimizing a phenotype with a specialized prediction model described herein.

All of the software stored within memory 1101 can be stored as a computer-readable instructions, that when executed by one or more processors 1102, cause the processors to perform the functionality described with respect to FIGS. 1-10.

Processor(s) 1102 execute computer-executable instructions and can be a real or virtual processors. In a multi-processing system, multiple processors or multicore processors can be used to execute computer-executable instructions to increase processing power and/or to execute certain software in parallel. As discussed earlier in the application, processors can be processors specialized for the task of training and applying a predictive model, such as graphical processing units (GPUs).

Computing environment 1100 additionally includes a communication interface 1103, such as a network interface, which is used to communicate with devices, applications, or processes on a computer network or computing system, collect data from devices on a network, and implement encryption/decryption actions on network communications within the computer network or on data stored in databases of the computer network. The communication interface conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Computing environment 1100 further includes input and output interfaces 1304 that allow users (such as system administrators) to provide input to the controller to cause the neurological screening device to display information, to edit data stored in memory 1301, or to perform other administrative functions. For example, an administrator can configure, add, or edit, for example, constraints, encoding software, or experimental data points stored in memory 1101.

An interconnection mechanism (shown as a solid line in FIG. 11), such as a bus, controller, or network interconnects the components of the computing environment 1100.

Input and output interfaces 1104 can be coupled to input and output devices. For example, Universal Serial Bus (USB) ports can allow for the connection of a keyboard, mouse, pen, trackball, touch screen, or game controller, a voice input device, a scanning device, a digital camera, remote control, or another device that provides input to the computing environment.

The computing environment 1100 can additionally utilize a removable or non-removable storage, such as magnetic disks, magnetic tapes or cassettes, CD-ROMs, CD-RWs, DVDs, USB drives, or any other medium which can be used to store information and which can be accessed within the computing environment 1100.

Computing environment 1100 can be a set-top box, personal computer, or one or more servers, for example a farm of networked servers, a clustered server environment, or a cloud network of computing devices.

It will be appreciated by those skilled in the art that changes could be made to the embodiments described above without departing from the broad inventive concept thereof. For example, the steps or order of operation of one of the above-described methods could be rearranged or occur in a different series, as understood by those skilled in the art. It is understood, therefore, that this disclosure is not limited to the particular embodiments disclosed, but it is intended to cover modifications within the spirit and scope of the following claims.

The invention claimed is:

1. A method executed by one or more computing devices for efficiently optimizing a phenotype with a specialized prediction model, the method comprising:

training, by at least one of the one or more computing devices, a phenotype prediction model based at least in part on a plurality of experimental data points and one or more constraints, the plurality of experimental data points comprising the genotype information and corresponding phenotype information;

applying, by at least one of the one or more computing devices, the phenotype prediction model to a plurality of available genotypes corresponding to the one or more of constrains to generate a plurality of scores, the phenotype prediction model being configured to predict one or more phenotypic attributes of the plurality of available genotypes;

determining, by at least one of the one or more computing devices, a plurality of result genotypes based at least in part on a ranking of the plurality of available genotypes according to the plurality of scores; and generating, by at least one of the one or more computing devices, a result based at least in part on the plurality of result genotypes, the result indicating one or more genetic constructs for testing.

2. The method of claim 1, wherein the one or more constraints comprise the plurality of available genotypes and a plurality of desired phenotypic attributes.

3. The method of claim 1, wherein training a phenotype prediction model based at least in part on a plurality of experimental data points and one or more constraints comprises:

encoding genotype information in a plurality of experimental data points corresponding to the one or more constraints as a plurality of experiential genotype vectors; and training the phenotype prediction model based at least in part on the plurality of experiential genotype vectors, the corresponding phenotype information, and the one or more constraints.

4. The method of claim 3, wherein encoding genotype information in a plurality of experimental data points corresponding to the one or more constraints as a plurality of experiential genotype vectors comprises:

identifying the plurality of experimental data points in a database of experimental data points based at least in part on one or more of: at least one available genotype in the plurality of available genotypes or at least one desired phenotypic attribute in the plurality of desired phenotypic attributes; and encoding genotypes associated with the identified plurality of experimental data points as the plurality of experiential genotype vectors.

5. The method of claim 3, wherein training a phenotype prediction model based at least in part on the plurality of experiential genotype vectors, the phenotype information, and the one or more constraints comprises:

determining, by at least one of the one or more computing devices, one or more meta-parameters for the phenotype prediction model, the one or more meta-parameters being configured to maximize accuracy of the phenotype prediction model;

determining an objective function based at least in part on the plurality of desired phenotypic attributes; and iteratively adjusting the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

6. The method of claim 1, further comprising:

determining phenotype data corresponding to one or more result genotypes in the plurality of result genotypes; and updating, by at least one of the one or more computing devices, the plurality of experimental data points with the phenotype data and genotype data corresponding to the one or more result genotypes.

7. The method of claim 1, wherein the one or more phenotypic attributes comprise an ability to produce a specified molecule or compound, bacterial growth, or resistance of a strain to extreme conditions.

8. An apparatus for efficiently optimizing a phenotype with a specialized prediction model, the apparatus comprising:

one or more processors; and one or more memories operatively coupled to at least one of the one or more processors and having instructions stored thereon that, when executed by at least one of the one or more processors, cause at least one of the one or more processors to:

train a phenotype prediction model based at least in part on a plurality of experimental data points and one or more constraints, the plurality of experimental data points comprising the genotype information and corresponding phenotype information;

apply the phenotype prediction model to a plurality of available genotypes corresponding to the one or more of constrains to generate a plurality of scores, the phenotype prediction model being configured to predict one or more phenotypic attributes of the plurality of available genotypes;

determine a plurality of result genotypes based at least in part on a ranking of the plurality of available genotypes according to the plurality of scores; and generate a result based at least in part on the plurality of result genotypes, the result indicating one or more genetic constructs for testing.

9. The apparatus of claim 8, wherein the one or more constraints comprise the plurality of available genotypes and a plurality of desired phenotypic attributes.

10. The apparatus of claim 8, wherein the instructions that, when executed by at least one of the one or more processors, cause at least one of the one or more processors to train a phenotype prediction model based at least in part on a plurality of experimental data points and one or more constraints further cause at least one of the one or more processors to:

encode genotype information in a plurality of experimental data points corresponding to the one or more constraints as a plurality of experiential genotype vectors; and train the phenotype prediction model based at least in part on the plurality of experiential genotype vectors, the corresponding phenotype information, and the one or more constraints.

11. The apparatus of claim 10, wherein the instructions that, when executed by at least one of the one or more processors, cause at least one of the one or more processors to encode genotype information in a plurality of experimental data points corresponding to the one or more constraints as a plurality of experiential genotype vectors further cause at least one of the one or more processors to:

identify the plurality of experimental data points in a database of experimental data points based at least in part on one or more of: at least one available genotype in the plurality of available genotypes and at least one desired phenotypic attribute in the plurality of desired phenotypic attributes; and encode genotypes associated with the identified plurality of experimental data points as the plurality of experiential genotype vectors.

12. The apparatus of claim 10, wherein the instructions that, when executed by at least one of the one or more processors, cause at least one of the one or more processors to train a phenotype prediction model based at least in part on the plurality of experiential genotype vectors, the phenotype information, and the one or more constraints further cause at least one of the one or more processors to:

determine one or more meta-parameters for the phenotype prediction model, the one or more meta-parameters being configured to maximize accuracy of the phenotype prediction model;

determine an objective function based at least in part on the plurality of desired phenotypic attributes; and iteratively adjust the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

13. The apparatus of claim 8, wherein at least one of the one or more memories has further instructions stored thereon that, when executed by at least one of the one or more processors, cause at least one of the one or more processors to:
  determine phenotype data corresponding to one or more result genotypes in the plurality of result genotypes; and
  update the plurality of experimental data points with the phenotype data and genotype data corresponding to the one or more result genotypes.

14. The apparatus of claim 8, wherein the one or more phenotypic attributes comprise an ability to produce a specified molecule or compound, bacterial growth, or resistance of a strain to extreme conditions.

15. At least one non-transitory computer-readable medium storing computer-readable instructions for efficiently optimizing a phenotype with a specialized prediction model that, when executed by one or more computing devices, cause at least one of the one or more computing devices to:
  train a phenotype prediction model based at least in part on a plurality of experimental data points and one or more constraints, the plurality of experimental data points comprising the genotype information and corresponding phenotype information;
  apply the phenotype prediction model to a plurality of available genotypes corresponding to the one or more of constrains to generate a plurality of scores, the phenotype prediction model being configured to predict one or more phenotypic attributes of the plurality of available genotypes;
  determine a plurality of result genotypes based at least in part on a ranking of the plurality of available genotypes according to the plurality of scores; and
  generate a result based at least in part on the plurality of result genotypes, the result indicating one or more genetic constructs for testing.

16. The at one non-transitory computer-readable medium of claim 15, wherein the one or more constraints comprise the plurality of available genotypes and a plurality of desired phenotypic attributes.

17. The at one non-transitory computer-readable medium of claim 15, wherein the instructions that, when executed by at least one of the one or more computing devices, cause at least one of the one or more computing devices to train a phenotype prediction model based at least in part on a plurality of experimental data points and one or more constraints further cause at least one of the one or more computing devices to:
  encode genotype information in a plurality of experimental data points corresponding to the one or more constraints as a plurality of experiential genotype vectors; and
  train the phenotype prediction model based at least in part on the plurality of experiential genotype vectors, the corresponding phenotype information, and the one or more constraints.

18. The at one non-transitory computer-readable medium of claim 17, wherein the instructions that, when executed by at least one of the one or more computing devices, cause at least one of the one or more computing devices to encode genotype information in a plurality of experimental data points corresponding to the one or more constraints as a plurality of experiential genotype vectors further cause at least one of the one or more computing devices to:
  identify the plurality of experimental data points in a database of experimental data points based at least in part on one or more of: at least one available genotype in the plurality of available genotypes and at least one desired phenotypic attribute in the plurality of desired phenotypic attributes; and
  encode genotypes associated with the identified plurality of experimental data points as the plurality of experiential genotype vectors.

19. The at one non-transitory computer-readable medium of claim 17, wherein the instructions that, when executed by at least one of the one or more computing devices, cause at least one of the one or more computing devices to train a phenotype prediction model based at least in part on the plurality of experiential genotype vectors, the phenotype information, and the one or more constraints further cause at least one of the one or more computing devices to:
  determine one or more meta-parameters for the phenotype prediction model, the one or more meta-parameters being configured to maximize accuracy of the phenotype prediction model;
  determine an objective function based at least in part on the plurality of desired phenotypic attributes; and
  iteratively adjust the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

20. The at one non-transitory computer-readable medium of claim 15, further storing computer-readable instructions that, when executed by at least one of the one or more computing devices, cause at least one of the one or more computing devices to:
  determine phenotype data corresponding to one or more result genotypes in the plurality of result genotypes; and
  update the plurality of experimental data points with the phenotype data and genotype data corresponding to the one or more result genotypes.

21. The at one non-transitory computer-readable medium of claim 15, wherein the one or more phenotypic attributes comprise an ability to produce a specified molecule or compound, bacterial growth, or resistance of a strain to extreme conditions.

* * * * *